United States Patent [19]

Yokokura et al.

[11] Patent Number: 4,645,305
[45] Date of Patent: Feb. 24, 1987

[54] LIQUID-CRYSTAL COMPOUND, LIQUID CRYSTAL COMPOSITION AND LIQUID CRYSTAL DISPLAY DEVICE

[75] Inventors: Hisao Yokokura; Susumu Era, both of Hitachi; Hidetoshi Abe, Katsuta; Tadao Nakata, Katsuta; Teruo Kitamura, Katsuta; Akio Mukoh, Mito, all of Japan

[73] Assignee: Hitachi, Ltd., Tokyo, Japan

[21] Appl. No.: 674,325

[22] Filed: Nov. 23, 1984

[30] Foreign Application Priority Data

Nov. 24, 1983 [JP] Japan .................................. 58-219378

[51] Int. Cl.[4] .......................... G02F 1/13; C09K 19/20
[52] U.S. Cl. .................................. 350/351; 252/299.5; 252/299.63; 252/299.65; 252/299.66; 252/299.67; 350/350 R; 350/350 S; 560/20; 560/21; 560/23; 560/59; 560/60; 560/61; 560/86; 560/88; 560/102; 560/106; 560/107; 560/108; 560/109; 560/126; 560/127; 560/138; 560/141
[58] Field of Search ........... 252/299.5, 299.63, 299.65, 252/299.66, 299.67; 350/350 R, 350 S, 351; 560/20, 21, 23, 59, 60, 61, 102, 106, 107, 108, 109, 85, 86, 88, 126, 127, 138, 141

[56] References Cited

U.S. PATENT DOCUMENTS

| | | | |
|---|---|---|---|
| 3,796,999 | 3/1974 | Kahn ................. | 252/299.63 |
| 3,925,238 | 12/1975 | Gavrilovic ............ | 252/299.65 |
| 3,951,846 | 4/1976 | Gavrilovic ............ | 252/299.65 |
| 3,960,752 | 6/1976 | Flanderman et al. .... | 252/299.67 |
| 4,013,582 | 3/1977 | Gavrilovic ............ | 252/299.63 |
| 4,027,950 | 9/1977 | Moritama et al. ...... | 252/299.5 |
| 4,029,595 | 6/1977 | Ross et al. ........... | 252/299.63 |
| 4,113,647 | 9/1978 | Coates et al. ......... | 252/299.62 |
| 4,162,988 | 7/1979 | Maze et al. ........... | 252/299.6 |
| 4,227,778 | 10/1980 | Raynes ................ | 252/299.65 |
| 4,473,487 | 9/1984 | Romer et al. ......... | 252/299.5 |

FOREIGN PATENT DOCUMENTS

| | | | |
|---|---|---|---|
| 105701 | 5/1974 | German Democratic Rep. .................. | 252/299.63 |
| 50-43074 | 4/1975 | Japan .................. | 252/299.67 |
| 54-148184 | 11/1979 | Japan .................. | 252/299.63 |
| 124264 | 3/1985 | Poland ................ | 252/299.67 |
| 2092169 | 8/1982 | United Kingdom ........ | 252/299.63 |

OTHER PUBLICATIONS

Demus, D., Nonemissive Electrooptic Displays, pp. 83-119 (1975).
Griffin, A. C., et al., JACS, vol. 100, No. 20, pp. 6329-6333 (1978).
Coates, D., et al., Mol. Cryst. Liq. Cryst., vol. 37, pp. 249-262 (1976).
Gray, G. W., et al., Liquid Crystals & Plastic Crystals, vol. 1, John Wiley & Sons, Inc., N.Y., pp. 115-125 (1974).
C.A., vol. 103, 151045q (1975).
C.A., vol. 100, 174376a (1984).
C.A., vol. 95, 211906z (1981).

*Primary Examiner*—Teddy S. Gron
*Attorney, Agent, or Firm*—Antonelli, Terry & Wands

[57] ABSTRACT

The present liquid crystal compounds are novel ester-type compounds showing a smectic liquid crystal phase and being capable of increasing a dielectric constant anisotropy, represented by the following general formula: $R-X_1-Y_1-X_2-Y_2-NO_2$, wherein R is an alkyl group; $X_1$ and $X_2$ are the same or different from each other and are group $-COO-$ and $-OOC-$, and when $X_1$ is group $-COO-$,

$Y_1$ is group 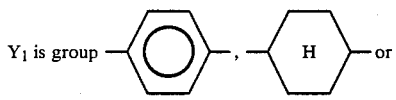 ,

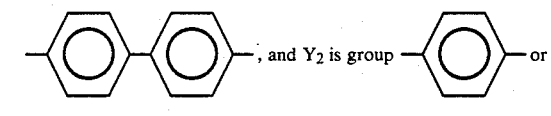

, and $Y_2$ is group

, and when $X_1$ is group $-OOC-$, (Abstract continued on next page.)

The present liquid composition contains the novel compound, and the present liquid crystal display device uses the liquid crystal composition for utilizing the characteristics of the novel compound. Particularly, the present liquid crystal display device is a thermally addressed display device.

9 Claims, 3 Drawing Figures

LIQUID-CRYSTAL COMPOUND, LIQUID CRYSTAL COMPOSITION AND LIQUID CRYSTAL DISPLAY DEVICE

BACKGROUND OF THE INVENTION

1. Field of the Invention

This invention relates to novel ester-type liquid crystal compounds, liquid crystal compositions containing the same liquid crystal compounds, and a liquid crystal display device provided with the same liquid crystal composition as a liquid crystal layer.

2. Description of the Prior Art

Heretofore, various display principles have been applied to electrooptical display devices using liquid crystals and practical liquid crystal devices have been already commercially available. Among others, TN type liquid crystal display devices using nematic liquid crystals with a twisting alignment have been widely utilized in wrist watches, table-type electronic computers, etc.

As to liquid crystal display devices having a desirable display system of higher precision and larger area to meet versatility of information, on the other hand, a thermally addressed system using a smectic liquid crystal to make display by mutual action between heat and electric field has been under study. Particularly, it has been regarded as very important to drive the thermally addressed devices using the smectic liquid crystal under a low potential with a low power in the same manner as TN-type liquid crystal display devices using the nematic liquid crystal, and it has been keenly desired to find liquid crystal compounds suitable for that purpose.

Generally, to lower the threshold potential (Vth) of liquid crystal corresponding to the working potential of a liquid crystal display device, it is necessary to increase a dielectric constant anisotropy ($\Delta\epsilon$) of the liquid crystal.

Known typical smectic liquid crystals having a relatively large, positive dielectric constant anisotropy are, for example, liquid crystal compounds represented by the following general formulae II and III:

(II)

wherein R' is a straight alkyl group having 8 to 12 carbon atoms, and

(III)

wherein R'O— is a straight alkoxy group having 8 to 12 carbon atoms, both of which will be hereinafter referred to "conventional type". However, the biphenyl-based liquid crystal compounds have such a disadvantage that the dielectric constant anisotropy as a physical property of liquid crystals is unsatisfactorily small.

SUMMARY OF THE INVENTION

An object of the present invention is to provide novel ester-type liquid crystal compounds showing a smectic liquid crystal phase and a large positive dielectric constant anisotropy, liquid crystal compositions containing the same liquid crystal compound as a component, and a liquid crystal display device provided with the same liquid crystal composition as a liquid crystal layer.

According to the first aspect of the present invention, liquid crystal compounds represented by the following general formula I are provided:

[I]

wherein R is an alkyl group; $X_1$ and $X_2$ are the same or different from each other and are groups —COO— or —OOC; when $X_1$ is the group —COO—, According to the second aspect of the present invention, liquid crystal compositions containing at least one of the liquid crystal compounds represented by the said general formula I are provided.

According to the third aspect of the present invention, a liquid crystal display device which comprises a liquid crystal layer between two counterposed electrode plates, where the liquid crystal layer is optically modulated by applying a potential between the electrode plates, characterized in that a liquid crystal composition constituting the liquid crystal layer is a liquid crystal composition containing at least one of the liquid crystal compounds represented by the general formula I.

Conventional type liquid crystal compounds whose 6-membered rings are directly bonded to one another have a small dielectric constant anisotropy. It has been found by the present inventors that the dielectric constant anisotropy of liquid crystal compounds can be made larger than that of the conventional type by inserting an ester group between the 6-membered rings themselves by bonding. However, it has been found that liquid crystal compounds having an ester group between the 6-membered rings themselves, as represented by the following general formula:

fail to show a smectic liquid crystal phase, and their dielectric constant anisotropy is not so large as expected.

The present inventors have made extensive studies of liquid crystal compounds showing a smectic liquid crystal phase and having a larger dielectric constant anisotropy from another viewpoint. As a result, it has been found that cyano group (—CN), etc. having a large dipole moment dielectric constant in the long axis direction of molecule have a larger dielectric constant anisotropy, but the liquid crystal compounds having the inserted cyano group hardly show the smectic liquid crystal phase. On the other hand, alkyl group (—R), alkoxy groups (—OR), etc. having a small dipole moment dielectric constant in the long axis direction of molecule have a smaller dielectric constant anisotropy, but are liable to show a smectic liquid crystal phase. That is, a contradicting tendency has been observed therebetween in the easiness to show a smectic liquid crystal phase and the direction to an increase in the dielectric constant anisotropy.

In view of the two requirements to show the smectic liquid crystal phase and increase the dielectric constant anisotropy and also from the viewpoint of anisotropy in the intramolecular force, the present inventors have tried to provide a nitro group (—NO$_2$) at one of non-cyclic groups directly bonded to the 6-membered ring in place of the cyano group and also to provide at another non-cyclic group an acyloxy group (RCO$_2$—) having the same effect as the ester group bonding the 6-membered rings themselves, and have prepared novel ester-type liquid crystal compounds taking into account an anisotropy in intramolecular force between the long axis direction and the short axis direction of molecule and have established the present invention.

When the acyloxy groups are provided at both terminals of non-cyclic terminal groups at both ends, the resulting liquid crystal compound is liable to turn a smectic liquid crystal and have a very small dielectric constant anisotropy. In the present invention, thus, the acyloxy group is provided only at one terminal thereof.

By providing the non-cyclic terminal groups at para positions of the 6-membered rings with respect to the bonding positions of the 6-membered rings themselves, the resulting liquid crystal molecule can be made linear, and the smectic liquid crystal phase can be shown better.

On the other hand, it is preferable that the acyloxy group provided at the non-cyclic terminal group has not more than 15 carbon atoms, since the smectic liquid crystal phase can be thereby also shown better.

The present liquid crystal compounds can be produced, for example, in the following manner:
Preparation of

An acid chloride RCOCl is condensed with by action of a base such as a mixture of benzene and pyridine to obtain

Thionyl chloride is added to the thus-obtained compound, and the mixture is heated under reflux to obtain an acid chloride. Excess thionyl chloride is completely removed from the reaction mixture by distillation under reduced pressure to obtain an acid chloride with the formula:

On the other hand, a cold solution of is prepared by dissolving it, for example, in a dissolvable amount of pyridine at room temperature, and a solution of the previously obtained acid chloride in an inert solvent is dropwised added to the cold solution with stirring and subjected to reaction at room temperature.

After the end of reaction, the reaction product is ice cooled and poured into water. After separation of the aqueous layer, the pyridine salt is washed. Then, the inert solvent is removed therefrom by distillation, and the residue is purified with an appropriate recrystallization solvent such as ethanol, etc., whereby is obtained as colorless crystals. The thus obtained compound can be used as a component for a liquid crystal composition showing a smectic liquid crystal phase and having a large positive dielectric constant anisotropy and is suitably applicable to a thermally addressed device capable of TN displaying in the manner shown in Application Example, particularly, displaying by mutual action between the heat and the electric field.

The present liquid crystal compositions can contain at least one of the said liquid crystal compounds above, or a mixture thereof with another liquid crystal compound, or further with other additives such as pigments, optically active substances, etc. Their mixing ratio can be selected as desired, but it is preferable that at least 5% by weight of the present liquid crystal compound should be contained on the basis of the mixture. In the case of mixing a liquid crystal compound having a positive dielectric constant anisotropy, TN displaying can be made, and in the case of mixing of a liquid crystal compound having a negative dielectric constant anisotropy and a dichroic pigment, a positive type color displaying can be made. Particularly, in the case of mixing a liquid crystal compound having a smectic phase and a large positive dielectric constant anisotropy, the resulting liquid crystal composition can be utilized in thermally addressed displaying by mutual action between the heat and the electric field. Furthermore, any desired display can be made by properly selecting additives.

DETAILED DESCRIPTION OF THE PREFERRED EMBODIMENTS

The present invention will be described in detail below, referring to Examples, which are not limitative of the present invention. Value of phase transition temperature is slightly fluctuated by measuring procedures and purity.

In the following Examples, the value of phase transition temperature in parentheses ( ) shows a monotropic transition temperature.

Figure 1:
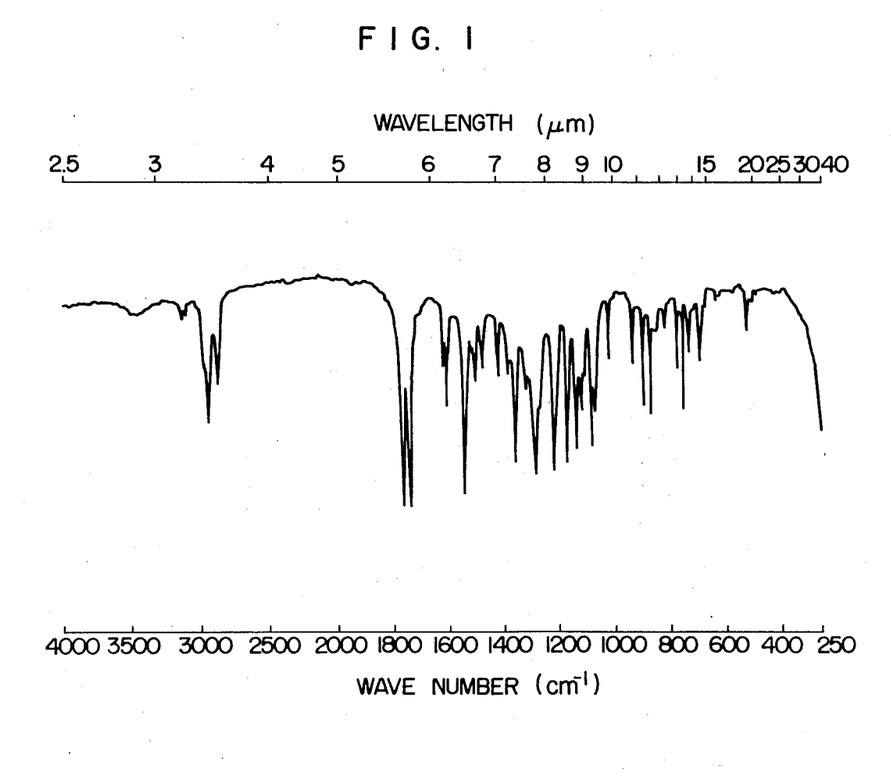
FIGS. 1 and 2 are infrared absorption spectrum diagrams of various liquid crystal compounds according to the present invention.
Figure 2:
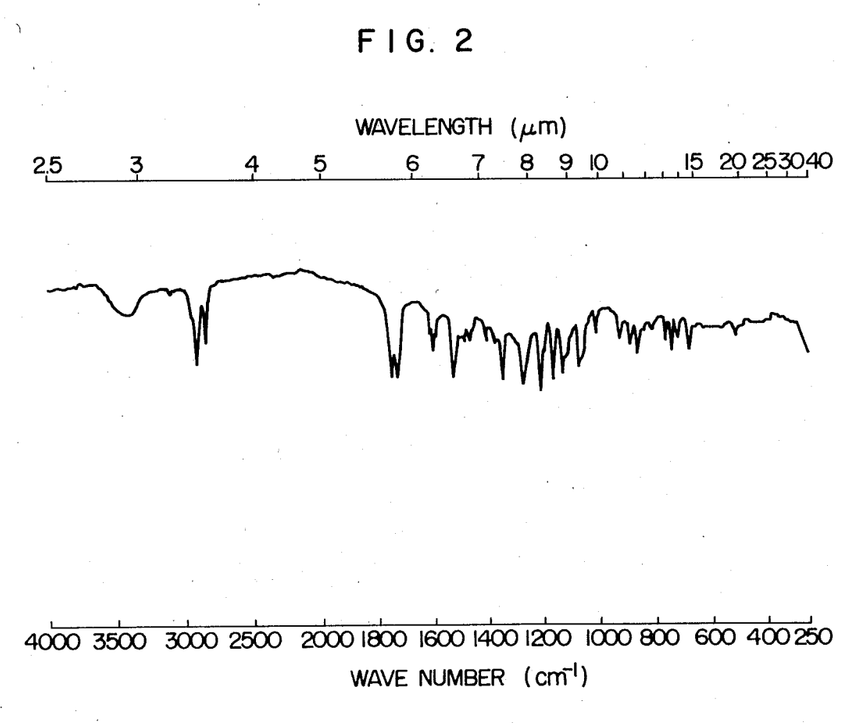

FIGS. 1 and 2 are infrared absorption spectrum diagrams of the present liquid crystal compositions.

EXAMPLE 1

Process for producing 4-nonanoyloxybenzoic acid-4'-nitrophenyl ester (abbreviated as 8AN) and its physical properties:

At first, 13.8 g (0.1 mole) of p-hydroxybenzoic acid was suspended in a benzene-pyridine mixture having a ratio of benzene:pyridine=10:0.1, which will be hereinafter used, while being cooled in ice. Then, 21.3 g (0.12 moles) of nonanoyl chloride was dropwise added thereto at a temperature of not more than 10° C. After the dropwise addition, the mixture was aged at 15° C. for 4 hours. After the aging, benzene and pyridine were removed therefrom by distillation under reduced pressure, and the residue was washed with water. After the washing with water, ether was added to the residue and then the resulting mixture was washed with water, and dried over $K_2CO_3$. Then, ether was removed therefrom by distillation, and the remaining crystals were recrystallized from ethanol, whereby was obtained as colorless crystals.
Then, 27.8 g (0.1 mole) of was dissolved in 50 ml of benzene and cooled in ice. Then, 23.8 g (0.2 moles) of excess thionyl chloride was added thereto, and the mixture was refluxed over a water bath at 60° C. to 70° C. for 3 hours. After the refluxing, excess thionyl chloride was removed therefrom by distillation, whereby was obtained.

On the other hand, 13.9 g (0.1 mole) of p-nitrophenol was suspended in a benzene-pyridine mixture while being cooled in ice, and then 35.6 g (0.12 moles) of previously prepared was dissolved in benzene at a temperature of not more than 10° C. and the resulting solution was dropwise added to the suspension. After the dropwise addition, the mixture was aged at 15° C. for 4 hours. After the aging, benzene and pyridine was removed therefrom by distillation under reduced pressure, and the residue was washed with water. After the washing with water, ether was added to the residue, and the resulting mixture was further washed with water, and dried over $K_2CO_3$. Then, ether was removed therefrom by distillation, and the remaining crystals were recrystallized from ethanol, whereby was obtained as colorless crystals. The thus obtained compound, i.e. 4-nonanoyloxybenzoic acid-4'-nitrophenyl ester, was a liquid crystal compound showing a nematic liquid crystal state at 55° to 69° C. (a smectic liquid crystal state at 51° C.). Its elemental analysis is shown below, and its infrared absorption spectrum is shown in FIG. 1.

|   | Found | Calculated | (as $C_{22}H_{25}NO_6$) |
|---|-------|------------|-------------------------|
| C | 66.18% | 66.16% | |
| H | 6.24% | 6.30% | |
| N | 3.48% | 3.51% | |

EXAMPLE 2

Preparation of 4-dodecanoyloxybenzoic acid-4-nitrophenyl ester (abbreviated as "11AN") and its physical properties:

At first, 13.8 g (0.1 mole) of p-hydroxybenzoic acid was suspended in a benzene-pyridine mixture while being cooled in ice. Then, 26.3 g (0.12 moles) of dodecanoyl chloride was dropwise added thereto at a temperature of not more than 10° C. After the dropwise addition, the mixture was aged at 15° C. for 4 hours. After the aging, benzene and pyridine were removed therefrom by distillation under reduced pressure, and the residue was washed with water. After the washing with water, ether was added thereto, and the mixture was washed with water and dried over $K_2CO_3$. Then, ether was removed therefrom by distillation, and the remaining crystals were recrystallized from ethanol, whereby was obtained as colorless crystal.

Then, 31.6 g (0.1 mole) of was dissolved in 50 ml of benzene, and the solution was cooled in ice. Furthermore, 23.8 g (0.2 moles) of thionyl chloride was added thereto, and the mixture was refluxed over an oil bath at 60° to 70° C. for 3 hours. After the refluxing, excess thionyl chloride was removed therefrom by distillation, whereby was obtained.

On the other hand, 13.9 g (0.1 mole) of p-nitrophenol was suspended in a benzene-pyridine mixture, while being cooled in ice. Then, 40.6 g (0.12 moles) of previously prepared was dissolved in benzene at a temperature of not more than 10° C., and the resulting solution was dropwise added to the suspension. After the dropwise addition, the mixture was aged at 15° C. for 4 hours. After the aging, benzene and pyridine were removed therefrom by distillation under reduced pressure, and the residue was washed with water. After the washing with water, ether was added to the residue, and the mixture was washed with water and dried over $K_2CO_3$. After the drying, ether was removed therefrom by distillation, and the remaining crystals were recrystallized from ethanol, whereby was obtained as colorless crystals. The thus obtained compound, i.e. 4-dodecanoyloxy benzoic acid-4'-nitrophenyl ester, was a liquid crystal compound showing a smectic liquid crystal state at 65° to 83° C., and its elemental analysis is given below:

|   | Found | Calculated | (as $C_{25}H_{31}NO_6$) |
|---|---|---|---|
| C | 68.10% | 68.02% |   |
| H | 7.11% | 7.07% |   |
| N | 3.16% | 3.17% |   |

EXAMPLE 3

4-tetradecanoyloxybenzoic acid-4'-nitrophenol ester (abbreviated as 13AN) and its physical properties:

At first, 13.8 g (0.1 mole) of p-hydroxybenzoic acid was suspended in a benzene-pyridine mixture while being cooled in ice. Then, 29.6 g (0.12 moles) of tetradecanoyl chloride was dropwise added thereto at a temperature of not more than 10° C. After the dropwise addition, the mixture was aged at 15° C. for 4 hours. After the aging, benzene and pyridine were removed therefrom by distillation under reduced pressure, and the residue was washed with water. After the washing with water, ether was added thereto, and the mixture was washed with water and dried over $K_2CO_3$. Then, ether was removed therefrom by distillation, and the remaining crystals were recrsytallized from ethanol, whereby was obtained as colorless crystal.

Then, 34.8 g (0.1 mole) of was dissolved in 50 ml of benzene, and the solution was cooled in ice. Furthermore, 23.8 g (0.2 moles) of thionyl chloride was added thereto, and the mixture was refluxed over an oil bath at 60° to 70° C. for 3 hours. After the refluxing, excess thionyl chloride was removed therefrom by distillation, whereby obtained.

On the other hand, 13.9 g (0.1 mole) of p-nitrophenol was suspended in a benzene-pyridine mixture, while being cooled in ice. Then, 44.0 g (0.12 moles) of previously prepared was dissolved in benzene at a temperature of not more than 10° C., and the resulting solution was dropwise added to the suspension. After the dropwise addition, the mixture was aged at 20° C. for 5 hours. After the aging, benzene and pyridine were removed therefrom by distillation under reduced pressure, and the residue was washed with water. After the washing with water, ether was added to the residue, and the mixture was washed with water and dried over $K_2CO_3$. After the drying, ether was removed therefrom by distillation, and the remaining crystals were recrystallized from ethanol, whereby was obtained as colorless crystals. The thus obtained compound, i.e. 4-tetradecanoyloxy benzoic acid-4'-nitrophenyl ester, was a liquid crystal compound showing a smectic liquid crystal state at 73° to 90° C., and its elemental analysis is given below, and its infrared absorption spectrum is shown in FIG. 2.

|   | Found | Calculated | (as $C_{27}H_{35}NO_6$) |
|---|---|---|---|
| C | 69.12% | 69.07% | |
| H | 7.51% | 7.51% | |
| N | 2.99% | 2.98% | |

The following compounds can be likewise obtained.
4-propanoyloxybenzoic acid-4-nitrophenyl ester,
4-butanoylonybenzoic acid-4-nitrophenyl ester,
4-pentanoyloxybenzoic acid-4-nitrophenyl ester,
4-hexanoyloxybenzoic acid-4-nitrophenyl ester,
4-heptanoyloxybenzoic acid-4-nitro phenyl ester,
4-decanoyloxybenzoic acid-4-nitrophenyl ester,
4-undecanoyloxybenzoic acid-4-nitrophenyl ester,
4-tridecanoyloxybenzoic acid-4-nitrophenyl ester,
4-pentadecanoyloxybenzoic acid-4-nitrophenyl ester, etc.

EXAMPLE 4

Preparation of

One mole of alcohol R—OH is condensed with ½ mole of under an action of a base such as a benzene-pyridine mixture to obtain

On the other hand, a cold solution of in a dissolvable amount of pyridine at room temperature is prepared, and a solution of the previously prepared acid chloride in an inert solvent is dropwise added to the cold solution with stirring and subjected to reaction at room temperature. After the end of reaction, the reaction product is ice-cooled, and poured into water. The aqueous layer is separated, and the pyridine salt is washed. Then, the inert solvent is removed therefrom by distillation, and the remaining crystals are purified with an appropriate recrystallization solvent, whereby is obtained as colorless crystals.

Examples of the thus prepared compounds are given below:
4-propoxycarbonylbenzoic acid-4-nitrophenyl ester,
4-butoxycarbonylbenzoic acid-4-nitrophenyl ester,
4-pentyloxycarbonylbenzoic acid-4-nitrophenyl ester,
4-hexyloxycarbonylbenzoic acid-4-nitrophenyl ester,
4-heptyloxycarbonylbenzoic acid-4-nitrophenyl ester,
4-octyloxycarbonylbenzoic acid-4-nitrophenyl ester,
4-nonyloxycarbonylbenzoic acid-4-nitrophenyl ester,
4-decyloxycarbonylbenzoic acid-4-nitrophenyl ester,
4-undecyloxycarbonylbenzoic acid-4-nitrophenyl ester,
4-dodecyloxycarbonylbenzoic acid-4-nitrophenyl ester,
4-tridecyloxycarbonylbenzoic acid-4-nitrophenyl ester,
4-tetradecyloxycarbonylbenzoic acid-4-nitrophenyl ester,
4-pentadecyloxycarbonylbenzoic acid-4-nitrophenyl ester, etc.

EXAMPLE 5

Preparation of

Thionyl chloride is added to and the mixture is heated under reflux to obtain an acid chloride. Excess thionyl chloride is completely removed from the reaction mixture by distillation under reduced pressure, whereby acid chloride is obtained.

On the other hand, a cold solution of in a dissolvable amount of pyridine at room temperature is prepared, and a solution of the previously prepared acid chloride in an inert solvent is dropwise added to the cold solution with stirring, and subjected to reaction at room temperature, whereby is obtained. Then, thionyl chloride is added thereto, and the mixture is heated under reflux to obtain an acid chloride. Excess thionyl chloride is completely removed from the reaction mixture by distillation under reduced pressure to obtain

Then, the thus obtained acid chloride is condensed with R—OH to obtain

Examples of the thus prepared compounds are given below:
4-nitrobenzoic acid-4-propoxycarbophenyl ester,
4-nitrobenzoic acid-4-butoxycarbonylphenyl ester,
4-nitrobenzoic acid-4-pentyloxycarbonylphenyl ester,
4-nitrobenzoic acid-4-hexyloxycarbonylphenyl ester,
4-nitrobenzoic acid-4-heptyloxycarbonylphenyl ester,
4-nitrobenzoic acid-4-octyloxycarbonylphenyl ester,
4-nitrobenzoic acid-4-nonyloxycarbonylphenyl ester,
4-nitrobenzoic acid-4-decyloxycarbonylphenyl ester,
4-nitrobenzoic acid-4-undecyloxycarbonylphenyl ester,
4-nitrobenzoic acid-4-dodecyloxycarbonyl phenyl ester,
4-nitrobenzoic acid-4-tridecyloxycarbonylphenyl ester,
4-nitrobenzoic adid-4-tetradecyloxycarbonylphenyl ester,
4-nitrobenzoic acid-4-pentadecyloxy carbonyl phenyl ester, etc.

EXAMPLE 6

Preparation of

One mole of acid chloride R—COCl is condensed with ½ mole of under an action of a base such as a benzene-pyridine mixtue to obtain

On the other hand, thionyl chloride is added to and the mixture is heated under reflux to obtain an acid chloride. Excess thionyl chloride is completely removed from the reaction mixture by distillation under reduced pressure to obtain an acid chloride A cold solution of previously obtained in a dissolvable amount of pyridine at room temperature is prepared, and a solution of the said acid chloride in an inert solvent is dropwise added to the cold solution with stirring and subjected reaction at room temperature.

After the end of reaction, the reaction product is ice-cooled and poured into water, and the aqueous layer is separated therefrom. The resulting pyridine salt is washed. Then, the inert solvent is removed therefrom by distillation, and the residue is purified with an appropriate recrystallization solvent, whereby is obtained as colorless crystals.

Examples of the thus obtained compounds are given below:
4-nitrobenzoic acid-4-propanoyloxydiphenyl ester,
4-nitrobenzoic acid-4-butanoyloxyphenyl ester,
4-nitrobenzoic acid-pentanoyloxy phenyl ester,
4-nitrobenzoic acid-hexanoyloxyphenyl ester,
4-nitrobenzoic acid-heptanoyloxyphenyl ester,
4-nitrobenzoic acid-octanoyloxyphenyl ester,

4-nitrobenzoic acid-nonanoyloxyphenyl ester,
4-nitrobenzoic acid-decanoyloxyphenyl ester,
4-nitrobenzoic acid-undecanoyloxyphenyl ester,
4-nitrobenzoic acid-dodecanoyloxyphenyl ester,
4-nitrobenzoic acid-tridecanoyloxyphenyl ester,
4-nitrobenzoic acid-tetradecanoyloxyphenyl ester,
4-nitrobenzoic acid-pentadecanoyloxy phenyl, ester,
etc.

EXAMPLE 7

Preparation of

Acid chloride RCOCl is condensed with under an action of a base such as a benzene-pyridine mixture to obtain

Then, thionyl chloride is added thereto, and the mixture is heated under reflux to obtain an acid chloride. Excess thionyl chloride is completely removed from the reaction mixture to obtain acid chloride On the other hand, a cold solution of in a dissolvable amount of pyridine at room temperature is prepared, and a solution of the previously prepared acid chloride in an inert solvent is dropwise added to the cold solution and subjected to reaction at room temperature. After the end of reaction, the reaction mixture was ice-cooled, and poured into water, and the aqueous layer is separated therefrom. The remaining pyridine salt is washed. Then, the inert solvent is removed therefrom by distillation, and the residue is purified with an appropriate recrystallization solvent, whereby is obtained as colorless crystals.

Examples of the thus prepared compounds are given below:

Trans-4-propanoyloxycyclohexanecarboxylic acid-4-nitrophenyl ester,
Trans-4-butanoyloxycyclohexanecarboxylic acid-4-nitrophenyl ester,
Trans-4-pentanoyloxycyclohexanecarboxylic acid-4-nitrophenyl ester,
Trans-4-hexanoyloxycyclohexanecarboxylic acid-4-nitrophenyl ester,
Trans-4-heptanoyloxycyclohexanecarboxylic acid-4-nitrophenyl ester,
Trans-4-octanoyloxycyclohexanecarboxylic acid-4-nitrophenyl ester,
Trans-4-nonanoyloxycyclohexanecarboxylic acid-4-nitrophenyl ester,
Trans-4-decanoyloxycyclohexanecarboxylic acid-4-nitrophenyl ester,
Trans-4-undecanoyloxycyclohexanecarboxylic acid-4-nitrophenyl ester,
Trans-4-tridecanoyloxycyclohexanecarboxylic acid-4-nitrophenyl ester,
Trans-4-tetradecanoyloxycyclohexanecarboxylic acid-4-nitrophenyl ester,
Trans-4-pentadecanoyloxycyclohexanecarboxylic acid-4-nitrophenyl ester, etc.

EXAMPLE 8

Preparation of

One mole of phenol R—OH is condensed with ½ mole of under an action of a base such as a benzene-pyridine mixture to obtain

On the other hand, a cold solution of in a dissolvable amount of pyridine at room temperature is prepared, and a solution of the previously prepared acid chloride in an inert solvent is dropwise added to the cold solution with stirring, and subjected to reaction at room temperature. After the end of reaction, the reaction mixture is ice-cooled and poured into water. The aqueous layer is separated therefrom, and the remaining pyridine salt is washed. Then, the inert solvent is removed therefrom by distillation, and the residue is purified with an appropriate recrystallization solvent, whereby is obtained as colorless crystals.

Examples of the thus prepared compounds are given below:

4-propoxycarbonylbenzoic acid-4-nitro-4'-biphenylyl ester,
4-butoxycarbonylbenzoic acid-4-nitro-4'-biphenylyl ester,
4-pentyloxycarbonylbenzoic acid-4-nitro-4'-biphenylyl ester,
4-hexyloxycarbonylbenzoic acid-4-nitro-4'-biphenylyl ester,
4-heptyloxycarbonylbenzoic acid-4-nitro-4'-biphenylyl ester,
4-octyloxycarbonylbenzoic acid-4-nitro-4'-biphenylyl ester,
4-nonyloxycarbonylbenzoic acid-4-nitro-4'-biphenylyl ester,
4-decyloxycarbonylbenzoic acid-4-nitro-4'-biphenylyl ester,
4-undecyloxycarbonylbenzoic acid-4-nitro-4'-biphenylyl ester,
4-dodecyloxycarbonylbenzoic acid-4-nitro-4'-biphenylyl ester,
4-tridecyloxycarbonylbenzoic acid-4-nitro-4'-biphenylyl ester,
4-tetradecyloxycarbonylbenzoic acid-4-nitro-4'-biphenyl ester,
4-pentadecyloxycarbonylbenzoic acid-4-nitro-4'-biphenylyl ester, etc.

EXAMPLE 9

Preparation of

Acid chloride RCOCl is condensed with under an action of a base such as a benzene-pyridine mixture to obtain

Thionyl chloride is added thereto, and the mixture is heated under reflux to obtain an acid chloride. Excess thionyl chloride is completely removed from the reaction mixture to obtain acid chloride On the other hand, a cold solution of in a dissolvable amount of pyridine at room temperature is prepared, and a solution of the previously prepared acid chloride in an inert solvent is added to the cold solution and subjected to reaction at room temperature. After the end of reaction, the reaction mixture is ice-cooled, and poured into water. The aqueous layer is separated therefrom, and the pyridine salt is washed. Then, the inert solvent is removed therefrom by distillation, and the residue is purified with an appropriate recrystallization solvent, whereby is obtained as colorless crystals.

Examples of the thus prepared compounds are given below:

4-propanoyloxybenzoic acid-4-nitro-4'-biphenylyl ester,
4-butanoyloxybenzoic-4-nitro-4'-biphenylyl ester,
4-pentanoyloxybenzoic acid-4-nitro-4'-biphenylyl ester,
4-hexanoyloxybenzoic acid-4-nitro-4'-biphenylyl ester,
4-heptanoyloxybenzoic acid-4-nitro-4'-biphenylyl ester,
4-octanoyloxybenzoic acid-4-nitro-4'-biphenylyl ester,
4-nonanoyloxybenzoic acid-4-nitro-4'-biphenylyl ester,
4-decanoyloxybenzoic acid-4-nitro-4'-biphenylyl ester,
4-undecanoyloxybenzoic acid-4-nitro-4'-biphenylyl ester,
4-dodecanoyloxybenzoic acid-4-nitro-4'-biphenylyl ester,
4-tridecanoyloxybenzoic acid-4-nitro-4'-biphenylyl ester,
4-tetradecanoyloxybenzoic acid-4-nitro-4'-biphenylyl ester,
4-pentadecanoyloxybenzoic acid-4-nitro-4'-biphenylyl ester, etc.

EXAMPLE 10

Preparation of

Acid chloride RCOCl is condensed with under an action of a base such as a benzene-pyridine mixture to obtain Then, thionyl chloride is added thereto and the mixture is heated under reflux to obtain an acid chloride. Excess thionyl chloride is completely removed therefrom by distillation under reduced pressure, whereby acid chloride is obtained.

On the other hand, a cold solution of in a dissolvable amount of pyridine at room temperature is prepared, and a solution of the previously prepared acid chloride in an inert solvent is dropwise added to the cold solution with stirring, and subjected to reaction at room temperature. After the end of reaction, the reaction product is ice-cooled, and poured into water. The aqueous layer is separated therefrom, and the remaining pyridine salt is washed. Then, the inert solvent is removed therefrom by distillation, and the residue is purified with an appropriate recrystallization solvent, whereby is obtained as colorless crystals.

Examples of the thus prepared compounds are given below:

4-propanoyloxy-4'-biphenylcarboxylic acid-4-nitrophenyl ester,
4-butanoyloxy-4'-biphenylcarboxylic acid-4-nitrophenyl ester,
4-pentanoyloxy-4'-biphenylcarboxylic acid-4-nitrophenyl ester,
4-hexanoyloxy-4'-biphenylcarboxylic acid-4-nitrophenyl ester,
4-heptanoyloxy-4'-biphenylcarboxylic acid-4-nitrophenyl ester,
4-octanoyloxy-4'-biphenylcarboxylic acid-4-nitrophenyl ester,
4-nonanoyloxy-4'-biphenylcarboxylic acid-4-nitrophenyl ester,
4-decanoyloxy-4'-biphenylcarboxylic acid-4-nitrophenyl ester,
4-undecanoyloxy-4'-biphenylcarboxylic acid-4-nitrophenyl ester,
4-dodecanoyloxy-4'-biphenylcarboxylic acid-4-nitrophenyl ester,
4-tridecanoyloxy-4'-biphenylcarboxylic acid-4-nitrophenyl ester,
4-tetradecanoyloxy-4'-biphenylcarboxylic acid-4-nitrophenyl ester,
4-pentadecanoyloxy-4'-biphenylcarboxylic acid-4-nitrophenyl ester, etc.

EXAMPLE 11

Conventional biphenyl-based liquid crystals, were mixed in a ratio of 1:1, and then mixed with 10, 20 and 30% by weight of the previously prepared liquid crystal compound 8AN to prepare compositions. Their phase transition temperature and dielectric constant anisotropy were measured. The results are shown in the following Table.

EXAMPLE 12

The conventional biphenyl-based liquid crystal mixture of Example 11 was mixed with 10, 20, and 30% by weight of the previously prepared liquid crystal compound 11AN to prepare compositions. Their phase transition temperature and dielectric constant anisotropy were measured. The results are shown in the following Table.

EXAMPLE 13

The conventional biphenyl-based liquid crystal mixture of Example 11 was mixed with 10, 20, and 30% by weight of the previously prepared liquid crystal compound 13AN to prepare compositions. Their phase transition temperature and dielectric constant anisotropy were measured. The results are shown in the following Table.

TABLE

| | Structural | Mixing ratio (wt. %) | Phase transition temperature (°C.) | Dielectric constant (20° C.) |
|---|---|---|---|---|
| Matrix liquid crystal mixture | $C_8H_{17}$—⟨◯⟩—⟨◯⟩—CN | 50 | $5.5 \overset{S}{\sim} 40 \overset{N}{\sim} 43$ | 7.4 |
| | $C_{10}H_{21}$—⟨◯⟩—⟨◯⟩—CN | 50 | | |
| 8AN | Matrix liquid crystal mixture + | 10 | $4 \overset{S}{\sim} 42 \overset{N}{\sim} 44$ | 10.0 |
| | | 20 | $3 \overset{S}{\sim} 43 \overset{N}{\sim} 45$ | 11.2 |
| | $C_8H_{17}CO_2$—⟨◯⟩—$CO_2$—⟨◯⟩—$NO_2$ | 30 | $2 \overset{S}{\sim} 44 \overset{N}{\sim} 46$ | 12.1 |
| 11AN | Matrix liquid crystal mixture + | 10 | $5 \overset{S}{\sim} 44 \overset{N}{\sim} 45$ | 10.2 |
| | | 20 | $5 \overset{S}{\sim} 47 \overset{N}{\sim} 48$ | 11.5 |
| | $C_{11}H_{23}CO_2$—⟨◯⟩—$CO_2$—⟨◯⟩—$NO_2$ | 30 | $5 \overset{S}{\sim} 49$ | 12.8 |
| 13AN | Matrix liquid crystal mixture + | 10 | $5 \overset{S}{\sim} 46 \overset{N}{\sim} 47$ | 9.8 |
| | | 20 | $5 \overset{S}{\sim} 49 \overset{N}{\sim} 50$ | 11.3 |
| | $C_{13}H_{27}CO_2$—⟨◯⟩—$CO_2$—⟨◯⟩—$NO_2$ | 30 | $5 \overset{S}{\sim} 52$ | 12.3 |

Remarks:
S: smectic phase
N: nemactic phase

As is evident from the foregoing table, liquid crystal compositions containing various liquid crystal compounds of the present invention have an effect of extending the smectic liquid crystal phase and increasing the dielectric constant anisotropy, whereas the conventional biphenyl-based liquid crystal mixture obviously has such a disadvantage that the dielectric constant anisotropy is no more increased.

EXAMPLE 14

Figure 3:
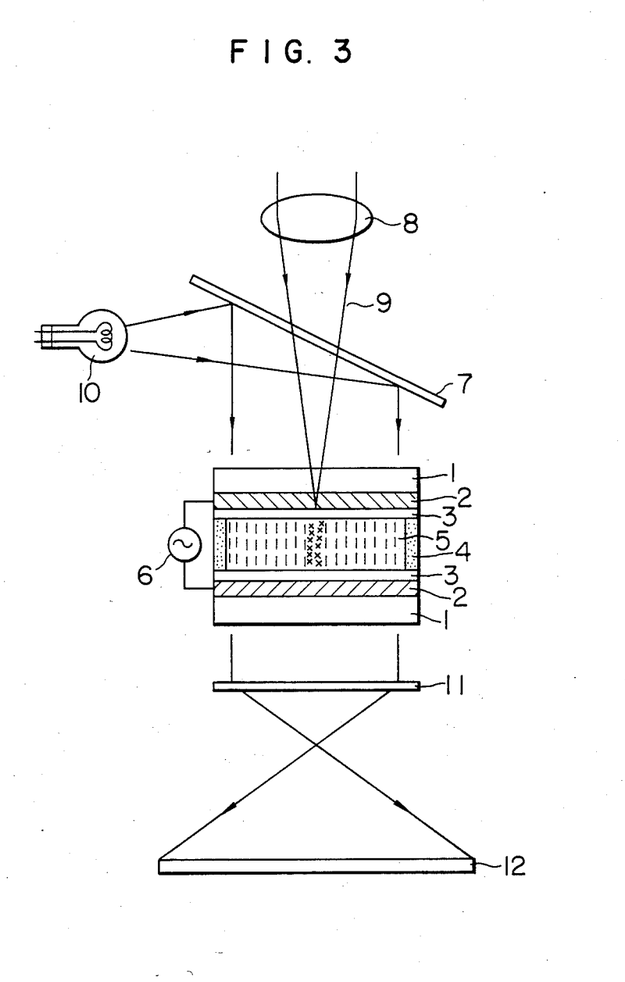
FIG. 3 is a schematic structural view of thermally addressed liquid crystal display device.

A thermally addressed liquid crystal display device having a structure shown in FIG. 3 was prepared with the liquid crystal composition of Example 11 containing 30% by weight of 8AN. FIG. 3 is a schematic structural diagram of a thermally addressed liquid display device, where numeral 1 is glass substrates, 2 transparent electrodes, 3 alignment films, 4 spacers, 5 smectic liquid crystal, 6 a power source, 7 a semi-transparent mirror, 8 a converging lens, 9 laser beam, 10 a white lamp, 11 a magnifying mirror, and 12 a screen. When the effacement total voltage of liquid crystal device was measured at a gap of 25 μm and a laser power of 72 μJ/dot, it was found that the their applicable 60 V could be lowered to 50 V.

As described above, the present novel ester-type liquid crystal compounds show a smectic liquid crystal phase and can increase a dielectric constant anisotropy, and an effacement total voltage of a thermally addressed liquid crystal display device using a liquid crystal composition containing the present liquid crystal compound can be effectively lowered.

What is claimed is:

1. A thermally addressed liquid crystal device comprising a liquid crystal layer between two counterposed electrodes at least one of which is transparent, a means for applying an electrical potential to the liquid crystal layer, and a means for heating a part of the liquid crystal layer, where the heated part of the liquid crystal layer is optically modulated against non-heated part of the liquid crystal layer, thereby making a display, the liquid crystal layer being a smectic liquid crystal composition containing a liquid crystal compound represented by the general formula:

wherein R is an alkyl group having 8 to 13 carbon atoms.

2. A liquid crystal device according to claim 1, wherein said liquid crystal composition contains at least 5% by weight of the liquid crystal compound.

3. A liquid crystal device according to claim 1, wherein the liquid crystal compound is 4-nonanoyloxybenzoic acid-4'-nitrophenyl ester.

4. A liquid crystal device according to claim 1, wherein the liquid crystal compound is 4-dodecanoyloxybenzoic acid-4-nitrophenyl ester.

5. A liquid crystal device according to claim 1, wherein the liquid crystal compound is 4-tetradecanoyloxybenzoic acid-4'-nitrophenyl ester.

6. A liquid crystal device according to claim 1, wherein said liquid crystal composition contains a mixture of -continued in a ratio of 1:1, said mixture being admixed with 10, 20 or 30% by weight of the liquid crystal compound.

7. A liquid crystal device according to claim 6, wherein the liquid crystal compound is 4-nonanoyloxybenzoic acid-4'-nitrophenyl ester.

8. A liquid crystal device according to claim 6, wherein the liquid crystal compound is 4-dodecanoyloxybenzoic acid-4-nitrophenyl ester.

9. A liquid crystal device according to claim 6, wherein the liquid crystal compound is 4-tetradecanoyloxybenzoic acid-4'-nitrophenyl ester.

* * * * *